United States Patent [19]

Porat et al.

[11] 4,205,674
[45] Jun. 3, 1980

[54] SURGICAL DRESSING

[76] Inventors: Michael Porat, 52 Hamitnadev St., Tel-Aviv Afeka; Amir Porat, 9 Keren Hayessod St., Ramat Ilan, Givat Shmuel, both of Israel

[21] Appl. No.: 826,975

[22] Filed: Aug. 23, 1977

[30] Foreign Application Priority Data

Aug. 24, 1976 [IL] Israel ............................ 50350

[51] Int. Cl.² .......................................... A61F 13/00
[52] U.S. Cl. .................................. 128/156; 128/169
[58] Field of Search ............... 128/169, 165, 155, 156, 128/327

[56] References Cited

U.S. PATENT DOCUMENTS

| | | | |
|---|---|---|---|
| 2,560,712 | 7/1951 | Bell | 128/165 X |
| 3,120,229 | 2/1964 | Hinkamp | 128/169 X |
| 3,233,608 | 2/1966 | Scaler, Jr. | 128/169 |
| 3,880,161 | 4/1975 | Fossel | 128/165 |

FOREIGN PATENT DOCUMENTS 1288916 12/1962 France ............................ 128/327

Primary Examiner—John D. Yasko
Attorney, Agent, or Firm—Harness, Dickey & Pierce

[57] ABSTRACT

A surgical dressing comprising an elastic bandage and a pad adapted to be attached to said bandage, a clasp being provided at one end of said bandage, all terms being within the meaning defined hereinabove.

1 Claim, 3 Drawing Figures

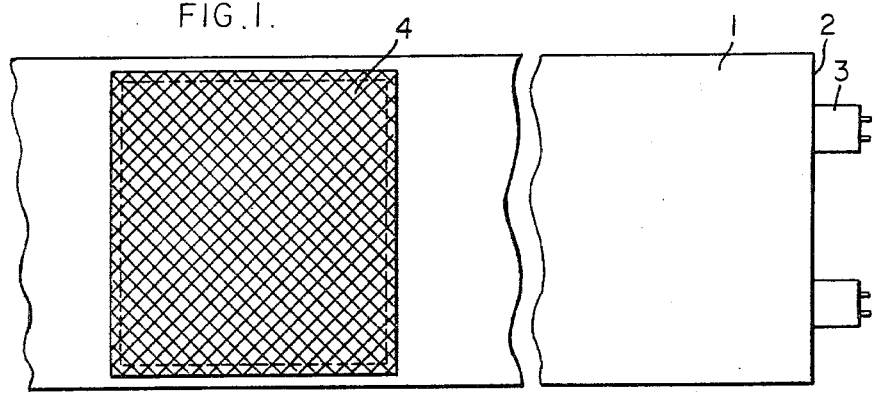
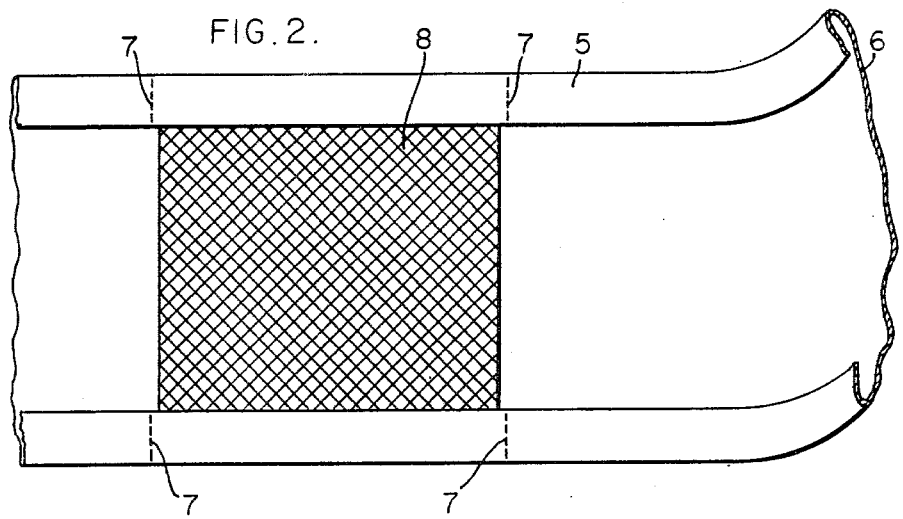
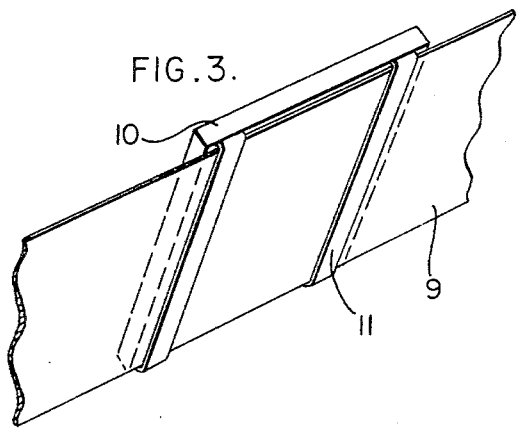

SURGICAL DRESSING

The present invention concerns surgical dressings, which may or may not be sterilized.

For the purpose of the following description and claims, the following definitions are given:

"ELASTIC BANDAGE": An elastic band variable in width and length, either woven or knitted or made by any other method, in any desired colour, made of cotton or any other elastic material, as known for surgical-dressing purposes (or non-dressing purposes).

"PAD": Swab, sponge, compress, made of gauze or any other material, filled with any absorbent material, or unfilled. It may be any other kind known or used in surgical-dressing, either adherent or non-adherent, medicated or not.

"CLASP": A means of securing the ends of the elastic bandage to the rest of the bandage, so that it will not open. It may be either a hook or hooks and/or any known adhering materials (e.g. Velcro TM) separable and/or reusable, as well as any other means applicable to the use of fastening elastic bandages.

It is the object of this invention to create a new surgical dressing for immediate use, which will secure a pad to a wound so that said pad will not move from its place during the movements of the body, as well as will protect the wound against external infection or any other further physical damage.

Today it is customary to dress the wound by the following different methods:

1. To put the pad on top of the wound and to bandage it with a gauze bandage.
2. To put the pad on top of the wound and to secure it with adhesive tape.
3. To use a pad sewn on a gauze bandage (first aid bandage).
4. To put the pad on top of the wound and bandage the pad and the wounded area with a knitted net (tube gauze), so that the pad will remain on the wound.

Each method mentioned above has advantages and disadvantages in comparison with the other methods:

(A) The gauze bandage protects the wound, but it becomes loose in a short time and the hold of the pad it thus not good. Especially if the wound is on one of the joints and when the members of the body move, the gauze bandage, since it does not permit easy movements, loosens and the pad moves from the wound. It is also difficult to dress unsymmetrical members (cone-like members). Two different items are needed:
 a. Gauze bandage.
 b. Gauze pad.
Each one of them has to be separately sterilized.

(B) The use of adhesive tape is not applicable to all the situations. There is a possibility of infection from the loose ends. The attachment of the tape loosens when perspiring and when applied to mobile members or joints and it does not really secure the pad to the wound. Again, there is the disadvantage of having to use two different items:
 a. Pad.
 b. Adhesive tape.

(C) The use of the first aid bandages has the same disadvantage as the use of gauze bandages, except for the fact that we use bandage and pad attached together and sterilized at the same time, and they are opened together for use.

(D) The use of knitted net bandages allow movement and completely secure the pad to the wound, but the disadvantage is that the material has to be cut each time, in order to fit it to the size of the wound. Likewise, the external protection of the pad is not perfect, as the net is not dense enough, and infection might get through easily.

Until today, elastic bandages are used, generally, for dressing various sprained and dislocated members or joints. Sometimes they are used to dress a wound located on a cone-like member, but they require a separate pad or dressing.

It is a further object of our invention to overcome all the disadvantages mentioned above.

Our invention is based on an elastic bandage, to which a pad is adapted to be attached by means of one of the methods described in the following. At one end of the bandage a clasp is provided and the entire unit can be wrapped in one packet, which may or may not be sterilized as desired.

The invention is illustrated, by way of example only, in the accompanying drawings in which:

FIGS. 1 and 2 show fragmentary plan views of two different embodiments of the surgical dressing according to the invention;

FIG. 3 is a fragmentary perspective view of a third embodiment.

In FIG. 1 an elastic bandage 1 of a given width is cut to any desired length and is provided at one free end 2 with two spaced clasps 3 as is known with elastic bandages. A pad 4 is attached by sewing to the bandage 1 at any suitable or desired position.

In order to pack the surgical dressing above described, the bandage 1 may be folded in zig-zag fashion or rolled from both ends up to the pad 4, or it may be rolled entirely and may be sterilized as one unit. It may be packed in any of the known systems.

Instead of sewing, the pad 4 to bandage 1, it may be attached thereto by permanent adhesive or by an adhesive which permits the removal of a used pad and substituting it by a new one. Furthermore, the pad need not be sewn all around its circumference, but may be sewn on two parallel sides only, or at certain points on its circumference, or in the four corners. If desired, the pad may be attached to the bandage by rivets or the like, it being understood that the material of the rivets has to be one which is medically accepted for use in dressings.

In the embodiment of the surgical dressing shown in FIG. 2, the longitudinal edges 5 of an elastic bandage 6 are folded over and pockets are formed by seams 7. Into these pockets, a pad 8 is loosely inserted by two of its opposed side edges. For the rest, i.e. clasps, folding, etc. this embodiment is similar to that described with reference to FIG. 1.

In the embodiment of the invention shown in FIG. 3, unto an elastic bandage 9 a pad 10 is threaded by means of spaced loops 11 sewn or otherwise fixed to the pad and straddling the bandage. Clasps (not shown) are provided at one end thereof. It can be seen that in this embodiment the pad can be moved to any suitable position on the bandage, or conversely, when the pad has been placed on a wound, the bandage can be moved relative to it for most conveniently bandaging it.

In order to use the surgical dressing above described, the wrapped package is opened to expose the pad and its absorbing side is placed on top of the wound and it tied thereon by stretching the elastic bandage into at least one round and attaching the end of the elastic bandage by its clasps to the rest of the bandage.

The advantages of our invention are as follows:
1. The pad stays always closed on the wound.
2. The bandaging is quick, easy and does not become loose, as at the end of the elastic bandage there is a clasp.
3. The elastic binding permits free movements without loosening the bandage, and without permitting the pad to move from its place.
4. The bandaging is simple and easy without any additional equipment.
5. One bandaging unit is provided, easy to use and store. There is the possibility to sterilize the pad with the elastic bandage and to wrap them in one unit package.
6. The bandaging of unsymmetrical parts of the body is made possible.
7. This invention does not require any expertise to form a good bandage.
8. A new first-aid dressing is created for quick bandaging purposes.

We claim:
1. A surgical dressing comprising an elastic bandage, said bandage being formed with a pocket by folding over and sewing edges of said bandage, an absorbent pad detachably attached to said bandage by insertion into said pocket, and a clasp affixed to one end of said bandage for securing said bandage to the body of a wearer with the pad in proximity to a wound.

* * * * *